(12) United States Patent
Knighton et al.

(10) Patent No.: US 10,507,012 B2
(45) Date of Patent: *Dec. 17, 2019

(54) VEIN HARVESTING SYSTEM AND METHOD

(71) Applicant: MAQUET Cardiovascular LLC, Mahwah, NJ (US)

(72) Inventors: David R. Knighton, Minneapolis, MN (US); Vance D. Fiegel, New Brighton, MN (US)

(73) Assignee: MAQUET CARDIOVASCULAR LLC, Mahwah, NJ (US)

( * ) Notice: Subject to any disclaimer, the term of this patent is extended or adjusted under 35 U.S.C. 154(b) by 431 days.

This patent is subject to a terminal disclaimer.

(21) Appl. No.: 14/298,752

(22) Filed: Jun. 6, 2014

(65) Prior Publication Data

US 2014/0371522 A1   Dec. 18, 2014

Related U.S. Application Data

(63) Continuation of application No. 13/348,387, filed on Jan. 11, 2012, now Pat. No. 8,777,835, which is a
(Continued)

(51) Int. Cl.
  *A61B 17/32*   (2006.01)
  *A61B 17/00*   (2006.01)
  *A61B 90/30*   (2016.01)

(52) U.S. Cl.
  CPC .............. *A61B 17/00008* (2013.01); *A61B 2017/00252* (2013.01); *A61B 2017/00969* (2013.01);
(Continued)

(58) Field of Classification Search
  CPC ...... A61B 17/0008; A61B 2017/00252; A61B 2017/00969; A61B 2034/302;
(Continued)

(56) References Cited

U.S. PATENT DOCUMENTS

| 1,083,386 A | 1/1914 | Chapman |
| 1,422,826 A | 7/1922 | Brown |

(Continued)

FOREIGN PATENT DOCUMENTS

| AU | 719712 B2 | 8/1997 |
| AU | 199935034 A1 | 1/2000 |

(Continued)

OTHER PUBLICATIONS

Dec. 8, 2005 Notification Concerning Transmittal of International Preliminary Report on Patentability (Chapter I of the Patent Cooperation Treaty) in PCT/US2004/015970 (9 pages).

(Continued)

*Primary Examiner* — Kim M Lewis
(74) *Attorney, Agent, or Firm* — Wesley Scott Ashton

(57) ABSTRACT

A tissue illumination system and a method for harvesting a section of a blood vessel from a patient's body for further use. The tissue illumination system includes a light catheter inserted into a lumen of the blood vessel section to illuminate the vessel section and vessel side branches with an intensity which is visible to the physician from an exterior of the vessel section and also includes a viewing element insertable into the lumen and capable of viewing the illuminated vessel section. The tissue illumination system also includes at least one tool insertable into the lumen and used to harvest the vessel section.

22 Claims, 5 Drawing Sheets

Related U.S. Application Data continuation of application No. 13/113,369, filed on May 23, 2011, now abandoned, which is a continuation of application No. 12/241,316, filed on Sep. 30, 2008, now Pat. No. 7,959,553, which is a continuation of application No. 11/787,323, filed on Apr. 16, 2007, now abandoned, which is a continuation of application No. 10/780,370, filed on Feb. 17, 2004, now Pat. No. 7,211,040, which is a continuation of application No. 10/391,148, filed on Mar. 18, 2003, now Pat. No. 6,705,986, which is a continuation of application No. 09/715,382, filed on Nov. 17, 2000, now Pat. No. 6,558,313.

(52) U.S. Cl.
CPC ..... *A61B 2090/306* (2016.02); *Y10S 623/916* (2013.01); *Y10S 623/917* (2013.01)

(58) Field of Classification Search
CPC ... A61B 17/56; A61B 2034/301; A61B 90/37; A61B 1/0669; A61B 2017/00261; A61B 5/150427; A61B 5/15186; Y10S 623/916; Y10S 623/917
USPC .......... 600/36; 606/170–172, 180, 189, 159, 606/160
See application file for complete search history.

(56) References Cited

U.S. PATENT DOCUMENTS

| | | |
|---|---|---|
| 1,683,708 A | 9/1928 | Wappler et al. |
| 1,727,495 A | 9/1929 | Wappler |
| 1,731,069 A | 10/1929 | Herman |
| 1,741,461 A | 12/1929 | Herman |
| 1,798,902 A | 3/1931 | Raney |
| 1,867,624 A | 7/1932 | Hoffman |
| 1,881,250 A | 10/1932 | Tomlinson |
| 1,978,495 A | 10/1934 | Landau |
| 2,001,169 A | 5/1935 | Wallace |
| 2,002,594 A | 5/1935 | Wappler et al. |
| 2,004,559 A | 6/1935 | Wappler et al. |
| 2,011,169 A | 8/1935 | Wappler |
| 2,012,937 A | 9/1935 | Beuoy |
| 2,028,635 A | 1/1936 | Wappler |
| 2,031,682 A | 2/1936 | Wappler et al. |
| 2,162,681 A | 6/1939 | Ryan |
| 2,220,720 A | 11/1940 | Jett |
| 2,227,727 A | 1/1941 | Leggiadro |
| 2,316,297 A | 4/1943 | Southerland et al. |
| 2,821,190 A | 1/1958 | Chase |
| 2,840,070 A | 6/1958 | Toffiemire |
| 2,868,206 A | 1/1959 | Stoesser |
| 2,944,552 A | 7/1960 | Cannon |
| 3,128,768 A * | 4/1964 | Geistauts ........... A61B 17/1633 408/112 |
| 3,168,096 A | 2/1965 | Brummelkamp |
| 3,185,155 A | 5/1965 | Slaten et al. |
| 3,200,028 A | 8/1965 | Chisholm |
| 3,224,320 A | 12/1965 | Knudsen |
| 3,297,022 A | 1/1967 | Wallace |
| 3,313,294 A | 4/1967 | Uddenberg |
| 3,336,916 A | 8/1967 | Edlich |
| 3,354,478 A | 11/1967 | Allen |
| 3,357,433 A | 12/1967 | Fourestier et al. |
| 3,391,690 A | 7/1968 | Armao |
| 3,439,523 A | 4/1969 | Wood |
| 3,568,677 A | 3/1971 | Nolan et al. |
| 3,613,682 A | 10/1971 | Naylor |
| 3,625,202 A | 12/1971 | Oyoshirhara |
| 3,772,127 A | 11/1973 | James |
| 3,805,793 A | 4/1974 | Wright |
| 3,835,841 A | 9/1974 | Terada |
| 3,856,016 A | 12/1974 | Davis |
| 3,857,386 A | 12/1974 | Ashbell |
| 3,866,599 A | 2/1975 | Johnson |
| 3,866,601 A | 2/1975 | Russell |
| 3,882,852 A | 5/1975 | Sinnreich |
| 3,882,854 A | 5/1975 | Hulka et al. |
| 3,929,137 A | 12/1975 | Gonser |
| 3,934,115 A | 1/1976 | Peterson |
| 3,938,527 A | 2/1976 | Rioux et al. |
| 3,980,861 A | 9/1976 | Fukunaga |
| RE29,088 E | 12/1976 | Shaw |
| 4,011,872 A | 3/1977 | Komiya |
| 4,030,743 A | 6/1977 | Warthen |
| 4,031,898 A | 6/1977 | Hiltebrandt et al. |
| 4,038,987 A | 8/1977 | Komiya |
| 4,052,980 A | 10/1977 | Grams et al. |
| 4,132,227 A | 1/1979 | Ibe |
| 4,175,545 A | 11/1979 | Termanini |
| 4,178,920 A | 12/1979 | Cawood, Jr. et al. |
| 4,190,042 A | 2/1980 | Sinnreich |
| 4,196,734 A | 4/1980 | Harris |
| 4,213,460 A | 7/1980 | Weiner |
| 4,232,660 A | 11/1980 | Coles |
| 4,248,214 A | 2/1981 | Hannah et al. |
| 4,257,420 A | 3/1981 | Terayama |
| 4,285,753 A | 8/1981 | Warthen |
| 4,315,510 A | 2/1982 | Kihn |
| 4,359,052 A | 11/1982 | Staub |
| 4,362,160 A | 12/1982 | Hiltebrandt |
| 4,369,768 A | 1/1983 | Vukovic |
| 4,370,980 A | 2/1983 | Lottick |
| 4,372,295 A | 2/1983 | Heckele |
| 4,418,692 A | 12/1983 | Guay |
| 4,423,727 A | 1/1984 | Widran et al. |
| 4,428,746 A | 1/1984 | Mendez |
| 4,440,170 A | 4/1984 | Golden et al. |
| 4,493,320 A | 1/1985 | Treat |
| 4,493,321 A | 1/1985 | Leather |
| 4,493,711 A | 1/1985 | Chin et al. |
| 4,499,898 A | 2/1985 | Knepshield et al. |
| 4,499,899 A | 2/1985 | Lyons, III |
| 4,516,574 A | 5/1985 | Hewes, Jr. |
| 4,516,575 A | 5/1985 | Gerhard et al. |
| 4,556,058 A | 12/1985 | Green |
| 4,557,255 A | 12/1985 | Goodman |
| 4,562,832 A | 1/1986 | Wilder et al. |
| 4,586,919 A | 5/1986 | Taheri |
| 4,587,968 A | 5/1986 | Price |
| 4,597,030 A | 6/1986 | Brody et al. |
| 4,597,379 A | 7/1986 | Kihn et al. |
| 4,597,389 A | 7/1986 | Ibrahim et al. |
| 4,600,940 A | 7/1986 | Sluyter |
| 4,607,622 A | 8/1986 | Fritch et al. |
| 4,638,802 A | 1/1987 | Okada |
| 4,646,738 A | 3/1987 | Trott |
| 4,649,917 A | 3/1987 | Karasawa |
| 4,651,733 A | 3/1987 | Mobin-Uddin |
| 4,653,476 A | 3/1987 | Bonnet |
| 4,654,024 A | 3/1987 | Crittenden et al. |
| 4,655,216 A | 4/1987 | Tischer |
| 4,656,999 A | 4/1987 | Storz |
| 4,657,018 A | 4/1987 | Hakky |
| 4,662,068 A | 5/1987 | Polonsky |
| 4,667,655 A | 5/1987 | Ogiu et al. |
| 4,671,274 A | 6/1987 | Sorochenko |
| 4,700,694 A | 10/1987 | Shishido |
| 4,702,246 A | 10/1987 | Ellis et al. |
| 4,705,041 A | 11/1987 | Kim |
| 4,726,370 A | 2/1988 | Karasawa et al. |
| 4,744,363 A | 5/1988 | Hasson |
| 4,745,908 A | 5/1988 | Wardle |
| 4,754,754 A | 7/1988 | Garito et al. |
| 4,759,348 A | 7/1988 | Cawood |
| 4,759,364 A | 7/1988 | Boebel |
| 4,762,120 A | 8/1988 | Hussein |
| 4,768,508 A | 9/1988 | Chin et al. |
| 4,772,093 A | 9/1988 | Abele et al. |
| 4,773,394 A | 9/1988 | Reichstein et al. |
| 4,779,611 A | 10/1988 | Grooters et al. |
| 4,793,346 A | 12/1988 | Mindich |

(56) References Cited

U.S. PATENT DOCUMENTS

| | | |
|---|---|---|
| 4,819,620 A | 4/1989 | Okutsu |
| 4,819,633 A | 4/1989 | Bauer et al. |
| 4,821,718 A | 4/1989 | Uldall |
| 4,838,246 A | 6/1989 | Hahn et al. |
| 4,858,595 A | 8/1989 | Buess et al. |
| 4,862,874 A | 9/1989 | Kellner |
| 4,865,019 A | 9/1989 | Phillips |
| 4,867,138 A | 9/1989 | Kubota et al. |
| 4,869,268 A | 9/1989 | Yoon |
| 4,874,375 A | 10/1989 | Ellison |
| 4,877,016 A | 10/1989 | Kantor et al. |
| 4,919,129 A | 4/1990 | Weber, Jr. et al. |
| 4,924,851 A | 5/1990 | Ognier et al. |
| 4,924,882 A | 5/1990 | Donovan |
| 4,931,042 A | 6/1990 | Holmes et al. |
| 4,932,952 A | 6/1990 | Wojciechowicz, Jr. |
| 4,936,842 A | 6/1990 | D'Amelio et al. |
| 4,950,278 A | 8/1990 | Sachse et al. |
| 4,959,067 A | 9/1990 | Muller |
| 4,966,596 A | 10/1990 | Kuntz et al. |
| 4,979,771 A | 12/1990 | Childs, III |
| 4,985,030 A | 1/1991 | Melzer et al. |
| 4,991,565 A | 2/1991 | Takahashi et al. |
| 4,994,062 A | 2/1991 | Nishigaki et al. |
| 4,997,419 A | 3/1991 | Lakatos et al. |
| 4,997,436 A | 3/1991 | Oberlander |
| 4,998,527 A | 3/1991 | Meyer |
| 4,998,972 A | 3/1991 | Chin et al. |
| 5,007,898 A | 4/1991 | Rosenbluth et al. |
| 5,007,907 A | 4/1991 | Nishigaki et al. |
| 5,007,908 A | 4/1991 | Rydell |
| 5,011,490 A | 4/1991 | Fischell et al. |
| 5,013,312 A | 5/1991 | Parins et al. |
| 5,020,514 A | 6/1991 | Heckele |
| 5,025,778 A | 6/1991 | Silverstein et al. |
| 5,026,370 A | 6/1991 | Lottick |
| 5,026,383 A | 6/1991 | Nobles |
| 5,035,232 A | 7/1991 | Lutze et al. |
| 5,037,433 A | 8/1991 | Wilk et al. |
| 5,046,251 A | 9/1991 | Scott |
| 5,047,038 A | 9/1991 | Peters et al. |
| 5,049,154 A | 9/1991 | Quadri |
| 5,053,041 A | 10/1991 | Ansari et al. |
| 5,100,420 A | 3/1992 | Green et al. |
| 5,122,137 A | 6/1992 | Lennox |
| 5,139,508 A | 8/1992 | Kantrowitz et al. |
| 5,147,356 A | 9/1992 | Bhatta |
| 5,151,096 A | 9/1992 | Khoury |
| 5,151,102 A | 9/1992 | Kamiyama et al. |
| 5,171,255 A | 12/1992 | Rydell |
| 5,171,311 A | 12/1992 | Rydell et al. |
| 5,181,919 A | 1/1993 | Bergman et al. |
| 5,188,630 A | 2/1993 | Christoudias |
| 5,190,541 A | 3/1993 | Abele et al. |
| 5,192,280 A | 3/1993 | Parins |
| 5,197,649 A | 3/1993 | Bessler et al. |
| 5,197,971 A | 3/1993 | Bonutti |
| 5,201,752 A | 4/1993 | Brown et al. |
| 5,203,773 A | 4/1993 | Green |
| 5,207,691 A | 5/1993 | Nardella |
| 5,213,093 A | 5/1993 | Swindle |
| 5,217,001 A | 6/1993 | Nakao et al. |
| 5,217,441 A | 6/1993 | Shichman |
| 5,217,458 A | 6/1993 | Parins |
| 5,226,890 A | 7/1993 | Ianniruberto et al. |
| 5,226,908 A | 7/1993 | Yoon |
| 5,230,621 A | 7/1993 | Jacoby |
| 5,250,046 A | 10/1993 | Lee |
| 5,251,613 A | 10/1993 | Adair |
| 5,258,006 A | 11/1993 | Rydell et al. |
| 5,259,366 A | 11/1993 | Reydel et al. |
| 5,267,998 A | 12/1993 | Hagen |
| 5,269,753 A | 12/1993 | Wilk |
| 5,269,785 A | 12/1993 | Bonutti |
| 5,271,380 A | 12/1993 | Riek et al. |
| 5,271,385 A | 12/1993 | Bailey |
| 5,273,026 A | 12/1993 | Wilk |
| 5,275,608 A | 1/1994 | Forman et al. |
| 5,276,306 A | 1/1994 | Huffman |
| 5,279,546 A | 1/1994 | Mische et al. |
| 5,279,565 A | 1/1994 | Klein et al. |
| 5,284,128 A | 2/1994 | Hart |
| 5,284,478 A | 2/1994 | Nobles et al. |
| 5,290,249 A | 3/1994 | Foster et al. |
| 5,290,284 A | 3/1994 | Adair |
| 5,290,286 A | 3/1994 | Parins |
| 5,295,994 A | 3/1994 | Bonutti |
| 5,300,036 A | 4/1994 | Mueller et al. |
| 5,312,423 A | 5/1994 | Rosenbluth et al. |
| 5,318,564 A | 6/1994 | Eggers |
| 5,318,586 A | 6/1994 | Ereren |
| 5,318,589 A * | 6/1994 | Lichtman ............... A61B 17/29 600/564 |
| 5,320,115 A | 6/1994 | Kenna |
| 5,322,503 A | 6/1994 | Desai |
| 5,330,497 A | 7/1994 | Freitas et al. |
| 5,334,150 A | 8/1994 | Kaali |
| 5,336,221 A | 8/1994 | Anderson |
| 5,336,229 A | 8/1994 | Noda |
| 5,336,231 A | 8/1994 | Adair |
| 5,337,736 A | 8/1994 | Reddy |
| 5,339,803 A | 8/1994 | Mayzels et al. |
| 5,345,927 A | 9/1994 | Bonutti |
| 5,346,504 A | 9/1994 | Ortiz et al. |
| 5,352,219 A | 10/1994 | Reddy |
| 5,352,222 A | 10/1994 | Rydell |
| 5,354,291 A | 10/1994 | Bales et al. |
| 5,359,995 A | 11/1994 | Sewell, Jr. |
| 5,360,428 A | 11/1994 | Hutchinson, Jr. |
| 5,366,476 A | 11/1994 | Noda |
| 5,368,015 A | 11/1994 | Wilk |
| 5,370,109 A | 12/1994 | Cuny |
| 5,373,840 A | 12/1994 | Knighton |
| 5,374,277 A | 12/1994 | Hassler |
| 5,376,076 A | 12/1994 | Kaali |
| 5,376,087 A | 12/1994 | Haber et al. |
| 5,380,291 A | 1/1995 | Kaali |
| 5,383,889 A | 1/1995 | Warner et al. |
| 5,385,572 A | 1/1995 | Nobles et al. |
| 5,386,817 A | 2/1995 | Jones |
| 5,386,818 A | 2/1995 | Schneebaum et al. |
| 5,389,098 A | 2/1995 | Tsuruta et al. |
| 5,391,178 A | 2/1995 | Yapor |
| 5,395,367 A | 3/1995 | Wilk |
| 5,395,383 A | 3/1995 | Adams et al. |
| 5,397,335 A | 3/1995 | Gresl et al. |
| 5,401,273 A | 3/1995 | Shippert |
| 5,403,312 A | 4/1995 | Yates et al. |
| 5,411,466 A | 5/1995 | Hess |
| 5,411,483 A | 5/1995 | Loomas et al. |
| 5,411,508 A | 5/1995 | Bessler et al. |
| 5,417,697 A | 5/1995 | Wilk et al. |
| 5,419,309 A | 5/1995 | Biehl |
| 5,423,321 A | 6/1995 | Fontenot |
| 5,423,813 A | 6/1995 | Kaiser et al. |
| 5,424,877 A | 6/1995 | Tsuyuki et al. |
| 5,425,355 A | 6/1995 | Kulick |
| 5,425,357 A | 6/1995 | Moll et al. |
| 5,431,151 A | 7/1995 | Riek et al. |
| 5,431,173 A * | 7/1995 | Chin ............... A61B 17/00234 128/898 |
| 5,441,041 A | 8/1995 | Sauer et al. |
| 5,441,044 A | 8/1995 | Tovey et al. |
| 5,441,497 A | 8/1995 | Narciso, Jr. |
| 5,441,498 A | 8/1995 | Perkins |
| 5,443,463 A | 8/1995 | Stern et al. |
| 5,445,638 A | 8/1995 | Rydell et al. |
| 5,447,502 A | 9/1995 | Haaga |
| 5,447,513 A | 9/1995 | Davison et al. |
| 5,448,990 A | 9/1995 | De Faria-Correa |
| 5,450,842 A | 9/1995 | Tovey et al. |
| 5,451,223 A | 9/1995 | Ben-Simhon |
| 5,452,513 A | 9/1995 | Zinnbauer et al. |
| 5,452,732 A | 9/1995 | Bircoll |

(56) References Cited

U.S. PATENT DOCUMENTS

| | | |
|---|---|---|
| 5,454,365 A | 10/1995 | Bonutti |
| 5,458,598 A | 10/1995 | Feinberg et al. |
| 5,460,629 A | 10/1995 | Shlain et al. |
| 5,468,248 A | 11/1995 | Chin et al. |
| 5,474,057 A | 12/1995 | Makower et al. |
| 5,480,409 A | 1/1996 | Riza |
| 5,486,155 A | 1/1996 | Muller et al. |
| 5,489,290 A | 2/1996 | Furnish |
| 5,490,836 A | 2/1996 | Desai |
| 5,496,317 A | 3/1996 | Goble et al. |
| 5,496,345 A | 3/1996 | Kieturakis et al. |
| 5,501,654 A | 3/1996 | Failla et al. |
| 5,505,686 A | 4/1996 | Willis et al. |
| 5,507,755 A | 4/1996 | Gresl et al. |
| 5,509,922 A | 4/1996 | Aranyi et al. |
| 5,511,564 A | 4/1996 | Wilk |
| 5,512,037 A | 4/1996 | Russell et al. |
| 5,512,721 A | 4/1996 | Young et al. |
| 5,514,151 A | 5/1996 | Fogarty et al. |
| 5,514,153 A | 5/1996 | Bonutti |
| 5,514,236 A | 5/1996 | Avellanet et al. |
| 5,522,830 A | 6/1996 | Aranyi |
| 5,527,331 A | 6/1996 | Kresch et al. |
| 5,533,496 A | 7/1996 | De Faria-Correa et al. |
| 5,535,759 A | 7/1996 | Wilk |
| 5,536,251 A | 7/1996 | Evard et al. |
| 5,540,711 A | 7/1996 | Kieturakis et al. |
| 5,549,605 A | 8/1996 | Hahnen |
| 5,549,636 A | 8/1996 | Li |
| 5,549,637 A | 8/1996 | Crainich |
| 5,551,947 A | 9/1996 | Kaali |
| 5,554,101 A | 9/1996 | Matula et al. |
| 5,556,563 A | 9/1996 | von der Heyde et al. |
| 5,558,620 A | 9/1996 | Heckele et al. |
| 5,564,615 A | 10/1996 | Bishop et al. |
| 5,565,122 A | 10/1996 | Zinnbauer et al. |
| 5,569,160 A | 10/1996 | Sauer et al. |
| 5,569,164 A | 10/1996 | Lurz |
| 5,569,183 A | 10/1996 | Kieturakis |
| 5,569,244 A | 10/1996 | Hahnen |
| 5,569,274 A | 10/1996 | Rapacki et al. |
| 5,569,291 A | 10/1996 | Privitera et al. |
| 5,571,100 A | 11/1996 | Goble et al. |
| 5,575,756 A | 11/1996 | Karasawa et al. |
| 5,582,611 A | 12/1996 | Tsuruta et al. |
| 5,588,581 A | 12/1996 | Conlon et al. |
| 5,591,183 A | 1/1997 | Chin |
| 5,591,186 A | 1/1997 | Wurster et al. |
| 5,593,418 A | 1/1997 | Mollenauer |
| 5,595,565 A | 1/1997 | Treat et al. |
| 5,599,349 A | 2/1997 | D'Amelio |
| 5,601,580 A | 2/1997 | Goldberg et al. |
| 5,601,581 A | 2/1997 | Fogarty et al. |
| 5,601,589 A | 2/1997 | Fogarty et al. |
| 5,601,601 A | 2/1997 | Tal et al. |
| 5,603,698 A | 2/1997 | Roberts et al. |
| 5,607,441 A | 3/1997 | Sierocuk et al. |
| 5,607,443 A | 3/1997 | Kieturakis et al. |
| 5,618,307 A | 4/1997 | Donlon et al. |
| 5,626,587 A | 5/1997 | Bishop et al. |
| 5,630,787 A | 5/1997 | Yabe et al. |
| 5,630,795 A | 5/1997 | Kuramoto et al. |
| 5,634,584 A | 6/1997 | Okorocha et al. |
| 5,634,924 A | 6/1997 | Turkel et al. |
| 5,647,871 A | 7/1997 | Levine et al. |
| 5,653,722 A | 8/1997 | Kieturakis |
| 5,653,726 A | 8/1997 | Kieturakis |
| 5,656,012 A | 8/1997 | Sienkiewicz |
| 5,658,282 A | 8/1997 | Daw et al. |
| 5,662,585 A | 9/1997 | Willis et al. |
| 5,662,588 A | 9/1997 | Iida |
| 5,662,662 A | 9/1997 | Bishop et al. |
| 5,665,085 A | 9/1997 | Nardella |
| 5,665,096 A | 9/1997 | Yoon |
| 5,667,480 A | 9/1997 | Knight et al. |
| 5,667,520 A | 9/1997 | Bonutti |
| 5,669,906 A | 9/1997 | Grossi et al. |
| 5,673,840 A | 10/1997 | Schulze et al. |
| 5,680,982 A | 10/1997 | Schulze et al. |
| 5,683,349 A | 11/1997 | Makower et al. |
| 5,685,820 A | 11/1997 | Riek et al. |
| 5,685,826 A | 11/1997 | Bonutti |
| 5,688,269 A | 11/1997 | Newton et al. |
| 5,688,270 A | 11/1997 | Yates et al. |
| 5,688,286 A | 11/1997 | Yoon |
| 5,690,606 A | 11/1997 | Slotman |
| 5,690,847 A | 11/1997 | La Valley et al. |
| 5,693,051 A | 12/1997 | Schulze et al. |
| 5,695,448 A | 12/1997 | Kimura et al. |
| 5,700,236 A | 12/1997 | Sauer et al. |
| 5,702,408 A | 12/1997 | Wales et al. |
| 5,702,412 A | 12/1997 | Popov et al. |
| 5,702,417 A | 12/1997 | Hermann |
| 5,704,372 A | 1/1998 | Moll et al. |
| 5,704,534 A | 1/1998 | Huitema et al. |
| 5,707,382 A | 1/1998 | Sierocuk et al. |
| 5,707,389 A | 1/1998 | Louw et al. |
| 5,707,390 A | 1/1998 | Bonutti |
| 5,709,680 A | 1/1998 | Yates et al. |
| 5,713,505 A | 2/1998 | Huitema |
| 5,716,325 A | 2/1998 | Bonutti |
| 5,716,352 A | 2/1998 | Viola et al. |
| 5,718,714 A | 2/1998 | Livneh |
| 5,720,761 A | 2/1998 | Kaali |
| 5,720,763 A | 2/1998 | Tovey |
| 5,722,934 A | 3/1998 | Knight et al. |
| 5,725,479 A | 3/1998 | Knight et al. |
| 5,728,119 A | 3/1998 | Smith et al. |
| 5,730,748 A | 3/1998 | Fogarty et al. |
| 5,730,756 A | 3/1998 | Kieturakis et al. |
| 5,735,848 A | 4/1998 | Yates et al. |
| 5,738,628 A | 4/1998 | Sierocuk et al. |
| 5,743,880 A | 4/1998 | Hlavka |
| 5,749,870 A | 5/1998 | Gloth et al. |
| 5,752,966 A | 5/1998 | Chang |
| 5,755,717 A | 5/1998 | Yates et al. |
| 5,759,150 A | 6/1998 | Konou et al. |
| 5,759,183 A | 6/1998 | VanDusseldorp |
| 5,759,188 A | 6/1998 | Yoon |
| 5,762,606 A | 6/1998 | Minnich |
| 5,766,169 A | 6/1998 | Fritzsch et al. |
| 5,766,215 A | 6/1998 | Muri et al. |
| 5,772,576 A | 6/1998 | Knighton et al. |
| 5,776,112 A | 7/1998 | Stephens et al. |
| 5,779,646 A | 7/1998 | Koblish et al. |
| 5,779,728 A | 7/1998 | Lunsford et al. |
| 5,782,753 A | 7/1998 | DeFonzo et al. |
| 5,795,331 A | 8/1998 | Cragg et al. |
| 5,797,907 A | 8/1998 | Clement |
| 5,797,920 A | 8/1998 | Kim |
| 5,807,393 A | 9/1998 | Williamson, IV et al. |
| 5,810,811 A | 9/1998 | Yates et al. |
| 5,814,016 A | 9/1998 | Valley et al. |
| 5,817,013 A | 10/1998 | Ginn et al. |
| 5,817,061 A | 10/1998 | Goodwin et al. |
| 5,817,062 A | 10/1998 | Flom et al. |
| 5,827,279 A | 10/1998 | Hughett et al. |
| 5,827,281 A | 10/1998 | Levin |
| 5,827,318 A | 10/1998 | Bonutti |
| 5,832,931 A | 11/1998 | Wachter et al. |
| 5,843,017 A | 12/1998 | Yoon |
| 5,843,121 A | 12/1998 | Yoon |
| 5,846,259 A * | 12/1998 | Berthiaume .......... A61M 25/00 606/191 |
| RE36,043 E | 1/1999 | Knighton |
| 5,857,961 A | 1/1999 | Vanden Hoek et al. |
| 5,860,997 A | 1/1999 | Bonutti |
| 5,868,785 A | 2/1999 | Tal et al. |
| 5,871,496 A | 2/1999 | Ginn et al. |
| 5,871,498 A | 2/1999 | Jervis et al. |
| 5,873,889 A | 2/1999 | Chin |
| 5,895,352 A | 4/1999 | Kleiner |
| 5,895,353 A | 4/1999 | Lunsford et al. |
| 5,897,487 A | 4/1999 | Ouchi |

(56) References Cited

U.S. PATENT DOCUMENTS

| | | | |
|---|---|---|---|
| 5,908,429 A | 6/1999 | Yoon |
| 5,913,870 A | 6/1999 | DeFonzo et al. |
| 5,914,062 A | 6/1999 | von der Heyde |
| 5,916,213 A | 6/1999 | Haissaguerre et al. |
| 5,916,233 A | 6/1999 | Chin |
| 5,921,993 A | 7/1999 | Yoon |
| 5,925,058 A | 7/1999 | Smith et al. |
| 5,928,135 A | 7/1999 | Knight et al. |
| 5,928,138 A | 7/1999 | Knight et al. |
| 5,928,264 A | 7/1999 | Sugarbaker et al. |
| 5,938,620 A | 8/1999 | Daxer |
| 5,944,732 A | 8/1999 | Raulerson et al. |
| 5,954,731 A | 9/1999 | Yoon |
| 5,957,923 A | 9/1999 | Hahnen et al. |
| 5,957,936 A | 9/1999 | Yoon et al. |
| 5,976,130 A | 11/1999 | McBrayer et al. |
| 5,980,549 A | 11/1999 | Chin |
| 5,984,937 A | 11/1999 | Morse et al. |
| 5,984,938 A | 11/1999 | Yoon |
| 5,984,939 A | 11/1999 | Yoon |
| 5,993,384 A | 11/1999 | Lunsford et al. |
| 5,997,570 A | 12/1999 | Ligtenberg et al. |
| 6,015,423 A | 1/2000 | Andrese |
| 6,036,713 A | 3/2000 | Kieturakis |
| 6,059,802 A | 5/2000 | Ginn |
| 6,071,232 A | 6/2000 | Knighton et al. |
| 6,077,277 A | 6/2000 | Mollenauer et al. |
| 6,080,102 A | 6/2000 | Konou et al. |
| 6,113,588 A | 9/2000 | Duhaylongsod et al. |
| 6,120,434 A | 9/2000 | Kimura et al. |
| 6,123,689 A | 9/2000 | To et al. |
| H1904 H | 10/2000 | Yates et al. |
| 6,129,661 A | 10/2000 | Iafrati et al. |
| 6,143,008 A | 11/2000 | Eaves, III |
| 6,162,173 A | 12/2000 | Chin et al. |
| 6,167,297 A | 12/2000 | Benaron |
| 6,176,825 B1 | 1/2001 | Chin et al. |
| 6,186,825 B1 | 2/2001 | Bogiel et al. |
| 6,193,653 B1 * | 2/2001 | Evans ............ A61B 17/00008 600/210 |
| 6,196,968 B1 | 3/2001 | Rydin et al. |
| 6,206,899 B1 | 3/2001 | Ginn |
| 6,228,025 B1 | 5/2001 | Hipps et al. |
| 6,234,958 B1 | 5/2001 | Snoke et al. |
| 6,270,492 B1 | 8/2001 | Sinofsky |
| 6,277,137 B1 | 8/2001 | Chin |
| 6,287,304 B1 | 9/2001 | Eggers et al. |
| 6,306,081 B1 | 10/2001 | Ishikawa et al. |
| 6,312,442 B1 | 11/2001 | Kieturakis et al. |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,361,543 B1 | 3/2002 | Chin et al. |
| 6,387,043 B1 | 5/2002 | Yoon |
| 6,406,425 B1 | 6/2002 | Chin et al. |
| 6,413,208 B1 | 7/2002 | Schollhorn et al. |
| 6,432,044 B1 | 8/2002 | Lunsford et al. |
| 6,432,115 B1 | 8/2002 | Mollenauer et al. |
| 6,471,638 B1 | 10/2002 | Chang et al. |
| 6,511,494 B1 | 1/2003 | Knighton et al. |
| 6,520,975 B2 | 2/2003 | Branco |
| 6,527,771 B1 | 3/2003 | Weadock et al. |
| 6,533,797 B1 | 3/2003 | Stone et al. |
| 6,544,260 B1 | 4/2003 | Markel et al. |
| 6,558,313 B1 * | 5/2003 | Knighton ......... A61B 17/00008 600/36 |
| 6,562,051 B1 | 5/2003 | Bolduc et al. |
| 6,592,604 B2 | 7/2003 | Hess et al. |
| 6,616,661 B2 | 9/2003 | Wellman et al. |
| 6,632,227 B2 | 10/2003 | Adams |
| 6,648,898 B1 | 11/2003 | Baxter |
| 6,656,176 B2 | 12/2003 | Hess et al. |
| 6,660,016 B2 | 12/2003 | Lindsay |
| 6,673,087 B1 | 1/2004 | Chang et al. |
| 6,699,180 B2 | 3/2004 | Kobayashi |
| 6,702,813 B1 | 3/2004 | Baxter et al. |
| 6,705,986 B2 * | 3/2004 | Fiegel ............ A61B 17/00008 128/898 |
| 6,730,020 B2 | 5/2004 | Peng et al. |
| 6,740,102 B2 | 5/2004 | Hess et al. |
| 6,749,609 B1 | 6/2004 | Lunsford et al. |
| 6,752,756 B2 | 6/2004 | Lunsford et al. |
| 6,762,368 B2 | 7/2004 | Saputro et al. |
| 6,811,546 B1 | 11/2004 | Callas et al. |
| 6,814,696 B1 | 11/2004 | Chang et al. |
| 6,814,743 B1 | 11/2004 | Chin et al. |
| 6,830,546 B1 | 12/2004 | Chin et al. |
| 6,884,248 B2 | 4/2005 | Bolduc et al. |
| 6,899,670 B2 | 5/2005 | Peng et al. |
| 6,951,568 B1 | 10/2005 | Chin |
| 6,963,792 B1 | 11/2005 | Green |
| 6,972,028 B2 | 12/2005 | Chin |
| 6,976,957 B1 | 12/2005 | Chin et al. |
| 7,033,357 B2 | 4/2006 | Baxter et al. |
| 7,066,875 B2 | 6/2006 | Knighton et al. |
| 7,097,665 B2 | 8/2006 | Stack et al. |
| 7,146,984 B2 | 12/2006 | Stack et al. |
| 7,211,040 B2 * | 5/2007 | Knighton ......... A61B 17/00008 128/898 |
| 7,214,180 B2 | 5/2007 | Chin |
| 7,226,409 B2 | 6/2007 | Peng et al. |
| 7,264,587 B2 | 9/2007 | Chin |
| 7,288,096 B2 | 10/2007 | Chin |
| 7,326,178 B1 | 2/2008 | Lunsford et al. |
| 7,344,536 B1 | 3/2008 | Lunsford et al. |
| 7,364,657 B2 | 4/2008 | Mandrusov et al. |
| 7,384,423 B1 | 6/2008 | Chin |
| 7,398,781 B1 | 7/2008 | Chin |
| 7,431,725 B2 | 10/2008 | Stack et al. |
| 7,476,198 B1 | 1/2009 | Chin et al. |
| 7,479,104 B2 | 1/2009 | Lau et al. |
| 7,485,092 B1 | 2/2009 | Stewart et al. |
| 7,534,243 B1 | 5/2009 | Chin et al. |
| 7,695,470 B1 | 4/2010 | Stewart et al. |
| 7,733,366 B2 | 6/2010 | Beavers et al. |
| 7,887,558 B2 | 2/2011 | Lin et al. |
| 7,938,842 B1 * | 5/2011 | Chin ............ A61B 17/00008 606/190 |
| 7,959,553 B2 * | 6/2011 | Knighton ......... A61B 17/00008 600/36 |
| 7,967,798 B2 | 6/2011 | Reydel et al. |
| 7,972,265 B1 * | 7/2011 | Chin ............ A61B 17/00008 600/206 |
| 7,981,133 B2 | 7/2011 | Chin |
| 8,075,559 B2 | 12/2011 | Stewart et al. |
| 8,777,835 B2 * | 7/2014 | Knighton ......... A61B 17/00008 600/36 |
| 2001/0021868 A1 | 9/2001 | Herbst et al. |
| 2001/0025177 A1 * | 9/2001 | Woloszko ............ A61B 18/12 606/41 |
| 2002/0128542 A1 | 9/2002 | Van Over |
| 2002/0183593 A1 | 12/2002 | Chin et al. |
| 2002/0193850 A1 | 12/2002 | Selman |
| 2003/0125719 A1 | 7/2003 | Furnish |
| 2003/0187460 A1 | 10/2003 | Chin et al. |
| 2003/0187461 A1 | 10/2003 | Chin |
| 2003/0236544 A1 | 12/2003 | Lunsford et al. |
| 2004/0097792 A1 | 5/2004 | Moll et al. |
| 2004/0102804 A1 | 5/2004 | Chin |
| 2004/0153098 A1 | 8/2004 | Chin et al. |
| 2004/0153101 A1 | 8/2004 | Bolduc et al. |
| 2004/0181242 A1 | 9/2004 | Stack et al. |
| 2004/0216748 A1 | 11/2004 | Chin |
| 2004/0236231 A1 | 11/2004 | Knighton et al. |
| 2004/0236310 A1 | 11/2004 | Chin et al. |
| 2005/0020911 A1 | 1/2005 | Viswanathan et al. |
| 2005/0192613 A1 | 9/2005 | Lindsay |
| 2005/0247320 A1 | 11/2005 | Stack et al. |
| 2005/0261712 A1 | 11/2005 | Balbierz et al. |
| 2005/0266109 A1 | 12/2005 | Chin et al. |
| 2005/0267499 A1 | 12/2005 | Stack et al. |
| 2005/0283380 A1 | 12/2005 | Garduno |
| 2006/0052660 A1 | 3/2006 | Chin |

(56) References Cited

U.S. PATENT DOCUMENTS

| | | |
|---|---|---|
| 2006/0074337 A1 | 4/2006 | Yoo |
| 2006/0079915 A1 | 4/2006 | Chin et al. |
| 2006/0116746 A1 | 6/2006 | Chin |
| 2006/0206121 A1 | 9/2006 | Chin et al. |
| 2006/0270900 A1 | 11/2006 | Chin et al. |
| 2006/0271032 A1 | 11/2006 | Chin et al. |
| 2006/0287574 A1 | 12/2006 | Chin |
| 2006/0287734 A1 | 12/2006 | Stack et al. |
| 2007/0060932 A1 | 3/2007 | Stack et al. |
| 2007/0118206 A1 | 5/2007 | Colgan et al. |
| 2007/0123799 A1 | 5/2007 | Meireles |
| 2007/0162067 A1 | 7/2007 | Lunsford et al. |
| 2007/0167692 A1 | 7/2007 | Kim |
| 2007/0198043 A1 | 8/2007 | Cox et al. |
| 2007/0219571 A1 | 9/2007 | Balbierz et al. |
| 2007/0238917 A1 | 10/2007 | Peng et al. |
| 2007/0276432 A1 | 11/2007 | Stack et al. |
| 2008/0039879 A1 | 2/2008 | Chin et al. |
| 2008/0065122 A1 | 3/2008 | Stack et al. |
| 2008/0097523 A1 | 4/2008 | Bolduc et al. |
| 2008/0103365 A1 | 5/2008 | Lunsford et al. |
| 2008/0132892 A1 | 6/2008 | Lunsford et al. |
| 2008/0145345 A1 | 6/2008 | Mandrusov et al. |
| 2008/0145469 A1 | 6/2008 | Chin et al. |
| 2008/0306333 A1 | 12/2008 | Chin |
| 2008/0306335 A1 | 12/2008 | Lau et al. |
| 2009/0023986 A1 | 1/2009 | Stewart et al. |
| 2009/0024156 A1 | 1/2009 | Chin |
| 2009/0062610 A1 | 3/2009 | Williams |
| 2009/0112122 A1 | 4/2009 | Chuang et al. |
| 2009/0281388 A1 | 11/2009 | Ito |
| 2009/0322513 A1 | 12/2009 | Hwang et al. |
| 2009/0326372 A1 | 12/2009 | Darlington et al. |
| 2010/0234843 A1 | 9/2010 | Stewart et al. |
| 2011/0202082 A1 | 8/2011 | Chin |
| 2012/0078037 A1 | 3/2012 | Stewart |

FOREIGN PATENT DOCUMENTS

| | | |
|---|---|---|
| AU | 199942354 A1 | 3/2000 |
| AU | 2007203086 A1 | 1/2009 |
| CA | 2244164 A1 | 7/1997 |
| CA | 2274270 A1 | 12/1999 |
| CA | 2279661 A1 | 2/2000 |
| CA | 2592766 A1 | 12/2008 |
| DE | 24669 | 10/1883 |
| DE | 40469 | 8/1887 |
| DE | 246691 | 5/1912 |
| DE | 24669 | 10/1956 |
| DE | H24669 | 10/1956 |
| DE | 2415263 A1 | 10/1975 |
| DE | 2550693 A1 | 5/1977 |
| DE | 3002088 A1 | 7/1981 |
| DE | 3525917 A1 | 2/1986 |
| DE | 39 42 589 A1 | 7/1991 |
| DE | 199 06 260 A1 | 9/1999 |
| DE | 198 27 360 A1 | 1/2000 |
| EP | 0131347 A2 | 1/1985 |
| EP | 0243714 A2 | 11/1987 |
| EP | 0341943 A2 | 11/1989 |
| EP | 0409569 A1 | 1/1991 |
| EP | 0517244 A1 | 12/1992 |
| EP | 0518230 A1 | 12/1992 |
| EP | 0664104 A2 | 7/1995 |
| EP | 0681811 A2 | 11/1995 |
| EP | 0409569 B1 | 1/1997 |
| EP | 0761171 A2 | 3/1997 |
| EP | 0769270 A1 | 4/1997 |
| EP | 0 845 244 A1 | 6/1998 |
| EP | 0867148 A1 | 9/1998 |
| EP | 0878168 A1 | 11/1998 |
| EP | 0979635 A2 | 2/2000 |
| EP | 0980673 A2 | 2/2000 |
| FR | 2265344 A1 | 10/1975 |
| GB | 2 082 459 A | 3/1982 |
| GB | 2 195 540 A | 4/1988 |
| JP | 0727043 A | 1/1995 |
| JP | 08117181 A | 5/1996 |
| JP | 2802244 B2 | 7/1998 |
| JP | 11172954 A | 6/1999 |
| JP | 11225282 A | 8/1999 |
| JP | 200037389 A | 2/2000 |
| JP | 200051221 A | 2/2000 |
| JP | 2007509702 A | 4/2007 |
| JP | 2007175478 A | 7/2007 |
| JP | 200911495 A | 1/2009 |
| RU | 639545 A | 12/1978 |
| RU | 1498474 A1 | 8/1989 |
| SU | 112367 | 4/1957 |
| SU | 510235 A1 | 4/1976 |
| SU | 1371689 A1 | 2/1988 |
| WO | 9108710 A1 | 6/1991 |
| WO | 9208513 A1 | 5/1992 |
| WO | 9220291 A1 | 11/1992 |
| WO | 9308754 A1 | 5/1993 |
| WO | 9418881 A1 | 9/1994 |
| WO | 9424949 A1 | 11/1994 |
| WO | 9424951 A1 | 11/1994 |
| WO | 9510982 A1 | 4/1995 |
| WO | 9519737 A1 | 7/1995 |
| WO | 9601130 A1 | 1/1996 |
| WO | 9630072 A1 | 10/1996 |
| WO | 9636287 A1 | 11/1996 |
| WO | 9716125 A1 | 5/1997 |
| WO | 9726831 A1 | 7/1997 |
| WO | 9733522 A1 | 9/1997 |
| WO | 9737701 A1 | 10/1997 |
| WO | 9802084 A2 | 1/1998 |
| WO | 9802102 A2 | 1/1998 |
| WO | 9806451 A1 | 2/1998 |
| WO | 9838935 A1 | 9/1998 |
| WO | 99/64109 A1 | 12/1999 |
| WO | 0040139 A1 | 7/2000 |
| WO | 0040160 A2 | 7/2000 |
| WO | 02/39882 A2 | 5/2002 |
| WO | 03057062 A2 | 7/2003 |
| WO | 03094758 A1 | 11/2003 |
| WO | 03105706 A1 | 12/2003 |
| WO | 2004066828 A2 | 8/2004 |
| WO | 2004066829 A2 | 8/2004 |
| WO | 2004073506 A2 | 9/2004 |
| WO | 2005006955 A2 | 1/2005 |
| WO | 2005044079 A2 | 5/2005 |
| WO | 2009036287 A1 | 3/2009 |

OTHER PUBLICATIONS

DeLaria et al., "Leg Wound Complications Associated with Coronary Revascularization," J. Thorac. Cardiovasc. Surg., 81:403-407 (1981).
Dimitri et al., "A Quick and Atraumatic Method of Autologous Vein Harvesting Using the Subcutaneous Extraluminal Dissector," J. Cardiovasc. Surg., 28:103-111 (1987).
Hauer et al., "Endoscopic Subfacial Discission of Perforating Veins," Surgical Endosc., 2:5-12 (1988).
"Incision Decision", Atrium Medical Corporation advertisement, appearing in J. Thorac. Cardiovasc. Surg., 83(4) (1982).
International Search Report dated Sep. 8, 2004 for International Application No. PCT/US2004/015970, including Written Opinion of the International Searching Authority (12 pages).
Meldrum-Hanna et al., "Long Saphaneous Vein Harvesting," J. Surg., 56:923-924 (1986).
Moazami et al., "Minimally Invasive Greater Saphenous Vein Harvesting for Coronary Artery Bypass Surgery," Surgical Rounds, pp. 94-98 (Mar. 1997).
Rashid et al., "Subcutaneous Technique for Saphenous Vein Harvest," Ann. Thorac. Surg., 37(2):169-170 (1984).
"Saphenous Vein Grafts are No. 1. Period.," Atrium Medical Corporation advertisement, appearing in J. Thorac. Cardiovasc. Surg., 81(6) (1981).
Wheatley, D.J., ed., Surgery of Coronary Artery Disease, C.V. Mosby Co., pp. 348-349, 374-375, Dec. 1986.

(56) References Cited

OTHER PUBLICATIONS

Jun. 28, 2002 PCT Search Report for corresponding International Application No. PCT/US01/45166 (2 pages).
Aug. 14, 2009 European Search Report for corresponding Application No. EP 01 99 6041.8 (3 pages).
Abbott et al., "Structural changes during preparation of autogenous venous grafts", Surgery, 1974, pp. 1031-1040, vol. 76, No. 6.
Berci, "Techniques for improving illumination and recording in endoscopy", Optics and Laser Technology, 1976, pp. 31-37.
Buchbinder et al., "Comparison of Patency Rate and Structural Changes of in Situ and Reversed Vein Arterial Bypass", Journal of Surgical Research, 1981, pp. 213-222, vol. 30.
Chin et al., "Technique Using the Fiberoptic Valvulotome for the in Situ Vein Graft", Surgery, Gynecology & Obstetrics, 1989, pp. 255-256.
Dregelid et al., "Endothelial cell injury in human saphenous veins after manipulation and tweezer grasping", The Journal of Cardio-vascular Surgery, 1988, pp. 464-469, vol. 29, No. 4.
Gundry et al., "Optimal preparation techniques for human saphenous vein grafts", Surgery, 1980, pp. 785-794, vol. 88, No. 6.
Johnson et al., "Endoscopic Femoral-Popliteal/Distal Bypass Grafting: A Preliminary Report", Journal American College of Surgeons, 1998, pp. 331-336, vol. 186, No. 3.
Knighton et al., "Saphenous Vein In Situ Bypass", The American Journal of Surgery, 1990, pp. 294-299, vol. 160.
Kyo et al., "Endoscopic harvest of saphenous vein graft for coronary artery bypass grafting: Saitama-Olympus technique", European Journal of Cardio-thoracic Surgery, 1998, pp. S93-S99, vol. 14, Suppl. 1.
Lamuraglia et al., "Angioscopy guided semiclosed technique for in situ bypass", Journal of Vascular Surgery, 1990, pp. 601-604, vol. 12, No. 5.
Matsumoto et al., "Direct Vision Valvulotomy in In Situ Venous Bypass", Surgery, Gynecology & Obstetrics, 1987, pp. 363-364, vol. 165.
Meldrum-Hanna et al., "An Improved Technique for Long Saphenous Vein Harvesting for Coronary Revascularization", The Annals of Thoracic Surgery, 1986, pp. 90-92, vol. 42, No. 1.
Pierik et al., "Subfascial Endoscopic Ligation in the Treatment of Incompetent Perforating Veins", European Journal of Vascular and Endovascular Surgery, 1995, pp. 38-41, vol. 9.
Stierli et al., "In situ femorodistal bypass: novel technique for angioscope-assisted intraluminal side-branch occlusion and valvulotomy. A preliminary report", British Journal of Surgery, 1991, 1376-1378, vol. 78, No. 11.
Weisstein, "Cone", From MathWorld—A Wolfram Web Resource. http://mathworld.wolfram.com/Cone.html, 3 pages, printed from the Internet Jan. 12, 2016.

* cited by examiner

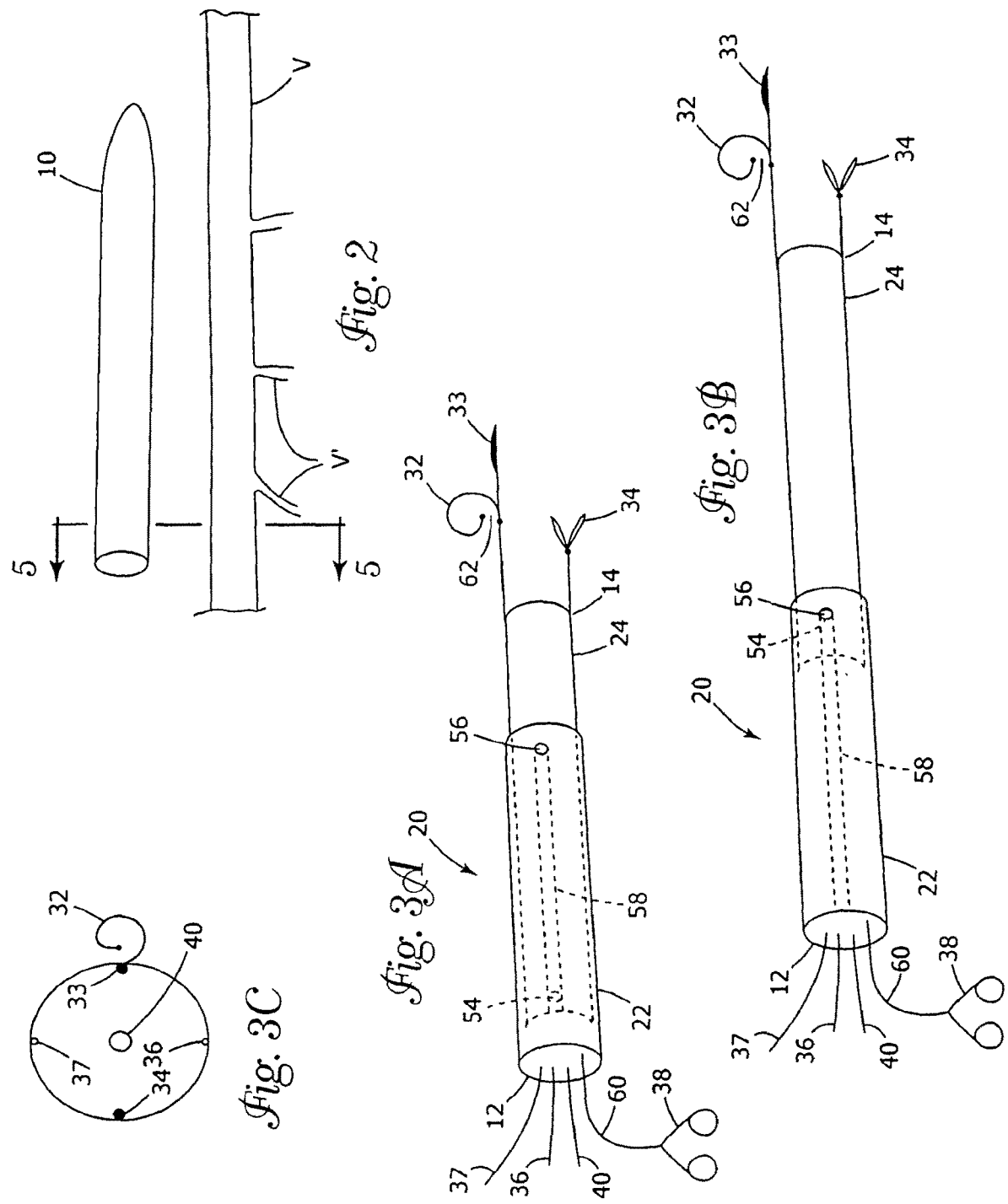

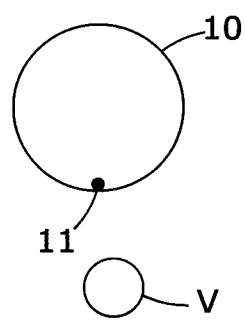
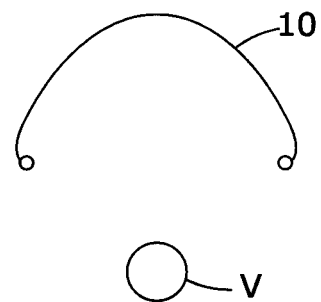
*Fig. 5A*  *Fig. 5B*
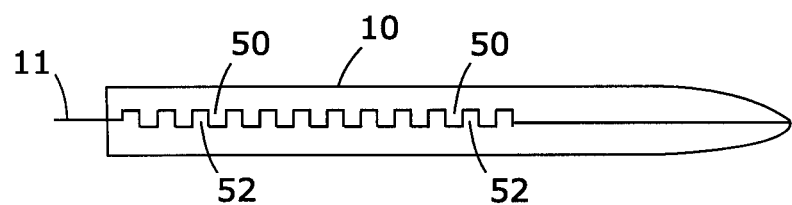
*Fig. 5C*

VEIN HARVESTING SYSTEM AND METHOD

This application is a continuation of application Ser. No. 13/348,387, filed Jan. 11, 2012, now U.S. Pat. No. 8,777,835, which is a continuation of application Ser. No. 13/113,369, filed May 23, 2011, now abandoned, which is a continuation of application Ser. No. 12/241,316, filed Sep. 30, 2008, now U.S. Pat. No. 7,959,553 B2, issued Jun. 14, 2011, which is a continuation of application Ser. No. 11/787,323, filed Apr. 16, 2007, now abandoned, which is a continuation of application Ser. No. 10/780,370, filed Feb. 17, 2004, now U.S. Pat. No. 7,211,040, issued May 1, 2007, which is a continuation of application Ser. No. 10/391,148, filed Mar. 18, 2003, now U.S. Pat. No. 6,705,986, issued Mar. 16, 2004, which is a continuation of application Ser. No. 09/715,382, filed Nov. 17, 2000, now U.S. Pat. No. 6,558,313, issued May 6, 2003, hereby incorporated herein by reference in its entirety.

FIELD OF THE INVENTION

This invention relates to a system and a method for harvesting a generally cylindrical tissue structure from the body of a patient. More particularly, the invention is directed to a system and a method for harvesting a section of a blood vessel from a patient.

BACKGROUND OF THE INVENTION

In certain circumstances it is desirable to remove sections of tubular tissue structure from a patient's body. Such tissue may be used in another part of the patient's body, may be transplanted into a second patient's body or may be discarded. As used herein, the term "tubular tissue structure" includes blood vessels, tendons, bile ducts, nerves and any other similar tissue formation which is generally tubular in structure and capable of being separated from surrounding tissue. Although the invention herein will be discussed in terms of harvesting blood vessels it should be understood that the apparatus and method described are equally applicable to harvesting other solid or cylindrical tubular tissue structure.

Vein harvesting is commonly done in connection with coronary artery bypass surgery. The saphenous vein is a subcutaneous vein which is often used for coronary artery bypass grafting, infra-inguinal bypass grafting and vein-vein bypass grafting. Other vessels may also be used including the internal mammary artery, the radial artery, and/or the lesser saphenous vein. Previously, it has been necessary to make an incision along the full length of the vein section to be removed. The vein is then freed by severing and ligating the branches of the vein, after which the section of the vein can be removed from the patient. The full-length incision must then be closed, for example by suturing or stapling. Obviously, the harvesting of the vein in this manner leaves disfiguring scars which are cosmetically undesirable. Additionally, the large incision creates a risk of infection to the patient and may not heal properly, especially with those patients who have poor circulation in their extremities. Such an incision may create a chronic non-healing wound, requiring significant and costly medical treatment.

Devices for harvesting a section of a blood vessel without creating a full-length incision have been suggested and include that described in U.S. Pat. No. 4,793,346 (Mindich) and UK Patent No. GB 20 82 459A. These patents describe methods that use incisions at either end of the blood vessel to be harvested. Such devices and methods can be disadvantageous because greater blood loss than is necessary can result. These devices may also remove more tissue than is necessary because the size of the cutting device is not readily adaptable to the changes in the size of the blood vessel. In addition, these patents describe techniques which have a high probability of damaging the vessel, making it unsuitable for use as a vascular conduit.

In U.S. Pat. No. RE 36,043 (Knighton), a device and a method for vein removal are disclosed which solve some of the problems associated with the use of prior art devices. Knighton discloses an endoscope having a lumen extending longitudinally through the scope body. The endoscope includes means for viewing an area adjacent the distal end of the lumen. The lumen has a lateral dimension large enough to accommodate the blood vessel being harvested and at least one tool for use in harvesting the blood vessel. A first end of the blood vessel section to be harvested is exposed through an incision in the patient's body. A dissecting tool and a gripping tool are inserted through the lumen of the endoscope and used to dissect the blood vessel away from the surrounding connective tissue of the patient's body. Additional tools are provided for use through the lumen of the endoscope to remove body fluids and coagulate bleeding tissue, to ligate and sever side branches from the blood vessel to be harvested, and to ligate and sever a distal end of the blood vessel to be harvested when a desired length of blood vessel has been dissected. Only a small incision in the patient's body is necessary to harvest a relatively long length of blood vessel in a precise and controlled manner using this device and procedure.

U.S. Pat. No. 5,772,576 (Knighton et al.) also describes a device and method for vein removal. The device has one or more lumens extending through a body portion. One lumen is sized to accommodate a blood vessel and at least one tool for use in removing the vessel. The device may also include viewing means so that the operator may remotely view an area adjacent the distal end of the body portion. The device protects the vessel being removed from damage by the tools used in the procedure, which is critical since the blood vessel is destined for reuse (as in arterial bypass). In addition, a single operator can use the device.

In commonly assigned, co-pending application Ser. No. 09/715,665, (Knighton et al.) filed Nov. 17, 2000, entitled "Vein Harvesting System and Method", the entirety of which is incorporated herein by reference, a system that is easier to use and minimizes damage to a blood vessel is described. In this system a multi-lumen tube is used in conjunction with a housing having a removable lower portion. The housing provides a workspace for the removal of a blood vessel and the multi-lumen tube and associated tools provide a means to see and to remove a desired length of vein and cut and cauterize any vein side branches while minimizing damage to the vein and trauma to the patient. An additional problem with present technology is determining the course of the main saphenous trunk versus a large side branch. The course of the main vein would also be beneficial to see well ahead of the dissection to facilitate the speed of dissection.

The need also exists for a vein harvester having a variable length and further having tools that would be easier and more convenient to use. The tools typically used in the current procedures tend to be long and difficult to control. Having tools with a variable length would allow for an easier, more precise, and more rapid procedure.

SUMMARY OF THE INVENTION

This invention is a system and a method for the harvesting of a blood vessel. The system comprises an expandable hood to make a workspace for extraction of the vein and an extendible or telescoping device having desired tools at its distal end. The tools are activated at the proximal end of the telescoping device. The method comprises illuminating the dissection area via a light catheter that is inside the lumen of the blood vessel and deploying the telescoping device to the length desired to dissect the vein from surrounding tissue.

In a first aspect the invention is a method of harvesting a section of a vessel from a human or animal body. The method comprises exposing the vessel section to be harvested through an incision in the body; providing a light source; placing the light source in the lumen of the vessel, the light source being sufficient to illuminate substantially the entire vessel section and vessel side branches extending from the vessel section with an intensity which is visible from an exterior of the vessel section; dissecting the vessel away from surrounding connective tissue of the body with a dissecting tool inserted through the incision; viewing the dissection of the vessel with a viewing element inserted through the incision; cutting the vessel at proximal and distal ends of the vessel section; and removing the vessel section from the patient's body. The vessel section may be exposed through first and second incisions with the dissecting tool and viewing element inserted through the first incision and the light source placed in the vessel lumen through the second incision. The first incision may be made over a proximal end of the vessel section and the second incision over a distal end of the vessel section. The method may further comprise providing a telescoping member having first and second substantially cylindrical segments, the second segment sized to fit within a lumen of the first segment, the telescoping member being adjustable in length from a fully collapsed position where the second segment is contained substantially within the first segment to a fully extended position where the second segment is substantially removed from the first segment, the telescoping member having the dissecting tool connected to a distal end of the second segment, and inserting the telescoping member through the incision. The step of proving the telescoping member may comprise providing a telescoping member wherein the viewing element and tool used to cut the vessel are connected to the distal end of the second segment. The method may comprise providing a hood member configured to be moveable from a first closed position to a second open position; inserting the hood member through the incision, adjacent the vessel; and creating a working space adjacent the vessel by opening the hood member from the first closed position to the second open position.

In another aspect the invention is a system for harvesting a section of a vessel from an incision in a human or animal body. The system comprises a light source sized and configured to be inserted into a lumen of the vessel, the light source being sufficient to illuminate substantially the entire vessel section with an intensity which is visible from an exterior of the vessel section; a viewing element configured to be insertable through the incision and capable of viewing the illuminated vessel section; and at least one tool used to harvest the vessel section, the at least one tool being sized to be inserted through the incision. This system may include a telescoping member having first and second substantially cylindrical segments, the second segment sized to fit within a lumen of the first segment, the telescoping member being adjustable in length from a fully collapsed position to a fully extended position by slidably adjusting the extent to which the second segment is contained in the lumen of the first segment, the telescoping element having a dissecting tool connected thereto. The viewing element may be connected to the telescoping member. A dissection element connected to the telescoping member may also be included. A hood member configured to be moveable from a first closed position to a second open position may be included in the system. The hood member is sized to be inserted through the incision in the closed position and placed adjacent the vessel section. The hood is further configured to create a working space adjacent the vessel when moved to the open position.

BRIEF DESCRIPTION OF THE DRAWINGS

FIG. 2 is a perspective view of the expandable hood in its retracted position over the vein to be harvested.

FIG. 3A is a perspective view of the telescoping device of the present invention in its retracted position.

FIG. 3B is a perspective view of the telescoping device of the present invention in its fully extended position.

FIG. 3C is an exploded view of the distal end of the telescoping device of FIGS. 3A and 3B.

FIG. 5A is a sectional view along line 5-5 of FIG. 2.

FIG. 5A is a sectional view along line 5-5 of FIG. 2.

FIG. 5B is a view similar to FIG. 5A but with expandable hood in its fully expanded position.

FIG. 5C is a bottom view of the expandable hood.

DETAILED DESCRIPTION OF THE INVENTION

The present invention is a system and a method for harvesting a tubular tissue section such as a section of a vessel from a patient's body for use in another part of a patient's body or for transplanting into a second patient's body. For example, a section of the saphenous vein may be removed for use in coronary bypass surgery. The saphenous vein travels along the medial side of the foot, leg, and thigh, where it joins with the femoral vein near the groin. Although specific reference herein is made to harvesting a section of saphenous vein it should be understood that the invention could be used to harvest other tubular tissue sections from human or animal bodies.

The terms "distal" and "proximal" as used herein refer to the method of use of the system. "Proximal" refers to a location closer to the physician and "distal" refers to a location farther from the physician. "Upper" and "lower" also are terms that refer to an orientation with respect to the use of the device, that is, relative to the physician.

In the method of this invention, the patient is first prepared for removal of the vein. The method is suitable for removal of any vein or tubular tissue structure; however, the invention is exemplified by reference to the saphenous vein. A first incision is made in the area from which the vein is to be harvested. For example, the incision is made in the groin area for harvesting the saphenous vein. A second, distal, incision is also made. For example, this distal incision will be near the knee (either above or below the joint) if the longest section possible of vein is needed. An expandable hood is inserted through the first incision and positioned over the top of the saphenous vein. This serves to lift surrounding tissue away from the vein. Then the expandable hood is expanded to create a space sufficient to permit the use of tools so that the vein may be dissected.

At the site of the distal incision, the vein or a side branch is cut and a light catheter (e.g., a fiber optic cable) is inserted into the lumen of the vein to illuminate the area of dissection and display the lumen of the vein. A device that is extendible, referred to as a telescoping device, is provided with tools at its distal end and is inserted through the first incision and under the expandable hood. The telescoping device provides the means to dissect the vein from the connective tissue and to cut and clip or cauterize any vein side branches. The telescopic device has a viewing fiber optic cable connected to a monitor so that the physician can see the dissection area. In addition, suction may be provided to remove blood and debris from the dissection field. Irrigation of the area of the vein with saline also may be provided through the telescoping device.

Figure 1:
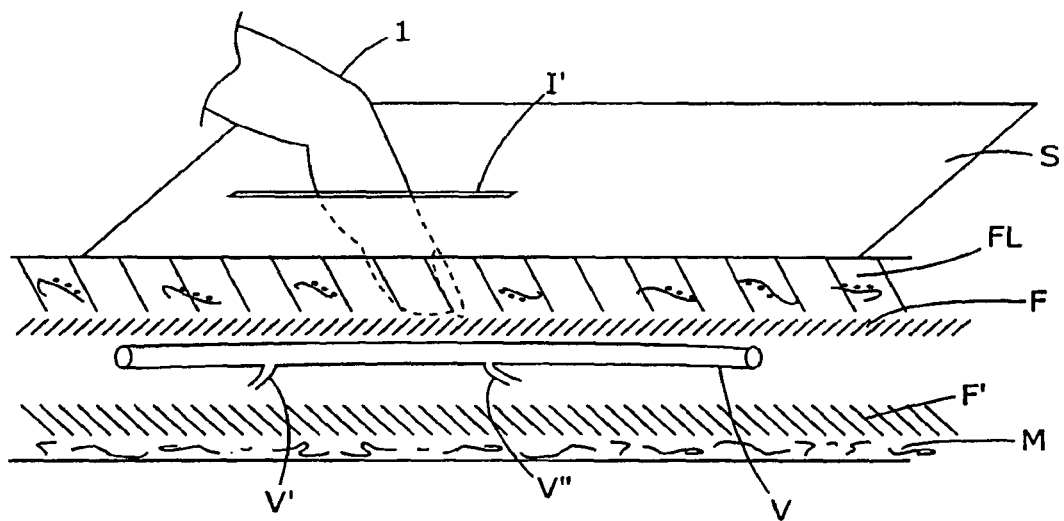
FIG. 1 is a partial cross-sectional view of a portion of a patient's body prepared for insertion of the device of the invention.

Turning now to the Figures, the system and method of the invention are illustrated. After proper preparation of the incision site, the physician makes a small incision I' (e.g., about 3 cm long) over the proximal aspect of the blood vessel to be harvested. FIG. 1 illustrates that incision I' is made in the region above the saphenous vein V. Vein V typically has side branches V'. The incision is made in the skin (S) and through various layers such as scarpa's fascia (F) and subcutaneous fat layer (FL). Underneath the saphenous vein is fascia (F') and muscle (M). For the sake of simplicity, such layers are not shown in FIGS. 2, 3A, 3B, 5A, 5B, and 6.

As shown in FIG. 1 the physician inserts a finger identified as reference numeral 1 to separate the various tissue layers from the saphenous vein and to make sufficient room to insert expandable hood 10 into incision I'. Hood 10 is inserted into the incision and moved distally a desired length of the saphenous vein. Optionally, a blunt dissector could be used to initially open a small space to allow for easier insertion of the hood. FIG. 5A is a cross-sectional view along line 5-5 in FIG. 2. In this position a portion of the proximal end of hood 10 extends from the incision. Hood 10 is now in a first closed or contracted position. Then hood 10 is expanded, or opened, as shown in cross-section in FIG. 5B. Hood 10 is opened to a second expanded position by removing pin 11 from the proximal end of the hood. The physician does this by simply grabbing and pulling on a proximal portion of the pin which extends from the hood. The hood is comprised of metal or plastic which is biased in the open or expanded direction. The pin 11 extends through holes in teeth 50 and 52 located on first and second lateral edges of the hood. As best seen in FIG. 5C in the closed position the teeth 50 and 52 mesh and are held together by the pin so that the hood remains in the closed position. Removal of pin 11 releases the lateral edges allowing the hood to expand to its open or expanded position. The movement of the hood from the closed to open position creates a sufficient working space above the saphenous vein for tools used in the harvesting procedure. Once the hood is expanded the site is ready to receive telescoping device 20.

Telescoping device 20 has proximal end 12 and distal end 14 and is constructed of a rigid material such as metal or plastic. Device 20 is shown in FIGS. 3A and 3B as having two telescoping segments, 22 and 24. It is to be understood that more telescoping segments could be used in the system of this invention depending on the length and degree of articulation desired. The length of one segment is shown as being about the same as the length of another segment, although it is also to be understood that the segments may have lengths different from one another.

Device 20 is advanced along the top of the saphenous vein under expandable hood 10 by extending the telescoping segments. FIG. 3A shows the device in a collapsed or non-extended condition with a substantial portion of segment 24 lying within segment 22. Segment 24 is sized to be friction fit within segment 22. The vein harvesting procedure is usually begun with the device in the collapsed position. As additional length is desired the device is withdrawn from the incision far enough so that the physician can grasp the two (or more) sections and pull them apart. The physician may adjust the relative position of the segments until the device has a desired length. The segments are friction fit in a manner that maintains the desired position between segments so that the device can continue to be used to dissect the vessel without axial slippage of the sections relative to one another. It will be appreciated that other means of extending the telescoping sections could be used such as using a worm gear and stepper motor. The segments are extended as the vein is dissected to the desired length, which is dependent upon the length of the vein to be dissected. As best seen in FIGS. 3A and 3B a spring-loaded dimple 54 on the proximal portion of segment 24 mates with a hole 56 in the distal portion of segment 22 to act as a positive stop of the relative movement between the sections. Alignment of dimple 54 with hole 56 may be accomplished by providing a longitudinal groove 58 on the inner surface of segment 22 in which dimple 54 is positioned. The longitudinal groove maintains the axial alignment of the segments as the device is extended. It will be apparent to those of skill in the art that other means of limiting the axial movement of the segments with respect to one another could be provided.

In FIG. 3A the device is shown in the collapsed position while in 3B the device is shown in the fully extended position. FIG. 3C shows a distal end view of the device and the various tools and viewing means connected thereto. Associated with telescoping device 20 are appropriate tools at distal end 14 which include vein dissector 32 and cutting means, such as bipolar scissors 34. Inserted through proximal end 12 is suction line 36, which is contained within central lumens of segments 22 and 24 and which provides a means to remove blood, debris, and irrigation fluid such as saline from the surgical area. Actuator 38 is operably connected through flexible line 60 to the bipolar scissors 34 and permits their operation at the desired time. Fiber optic line 40, or more generally an optical viewing device/detector, is provided to detect the light provided by the light catheter in the vein. The fiber optic line is connected to a monitor (not shown) so that the physician can see the dissection area. An irrigation line 37 is provided and connected to an irrigation source (not shown) at one end and to the distal end of the telescoping device at the other. Lines 36, 37, 40, and 60 extend from the proximal end of the device and are contained within the lumens of segments 22 and 24. Lines 36, 37, 40, and 60 are connected at the distal end of segment 22.

Vein dissector 32 is fixed at the end of segment 22, preferably at a circumferential position spaced approximately 180° from the position at which line 60 and bipolar scissors 34 are fixed. The vein dissector 32 is provided with an open loop having an opening 62 so that it can be slipped onto and off of the vein as desired. For example, during dissection of the vein if a side branch is encountered the vein dissector can be removed and the device rotated 180° so that the bipolar scissors can be used to cut and coagulate the side branch. The device is then rotated back and the vein dissector slipped over the vein and advanced in the distal direction so the dissection process is continued. Although a spacing of 180° is preferred between the vein dissector and bipolar scissors it will be appreciated that other spacing could be used so long as the spacing is sufficient to allow the tools to be used without interference from one another. Vein dissector 32 includes a blunt tip portion 33 which is used as an additional means of dissecting tissue from the vein and as a probe. This vein dissector may be a full circular dissector or, more preferably, a loop dissector as shown, which permits the vein to be dissected and removed from the dissector any time it is desired.

Cutting means 34 preferably is a bipolar scissors. Such scissors are configured to cut and cauterize size branches V' of the vein as they are encountered during the dissection of vein V. Alternatively, any cutting means can be used and appropriate ligation means (such as a suture or a clip) also can be used.

The actuator is adapted to operate cutting means 34, preferably bipolar scissors, which cuts and cauterizes side branches V' of vein V as the dissection proceeds. The dissection process proceeds distally along blood vessel V. The operator of the device views the dissection process (occurring at the area immediately adjacent distal end 14 of telescoping device 20) through the optical viewing device/detector, such as via fiber optic line 40, and associated monitor. Optionally, a saline infusion line 37 may be included to ensure that the lens at the distal end of the fiber optic line remains clear.

Figure 4A:
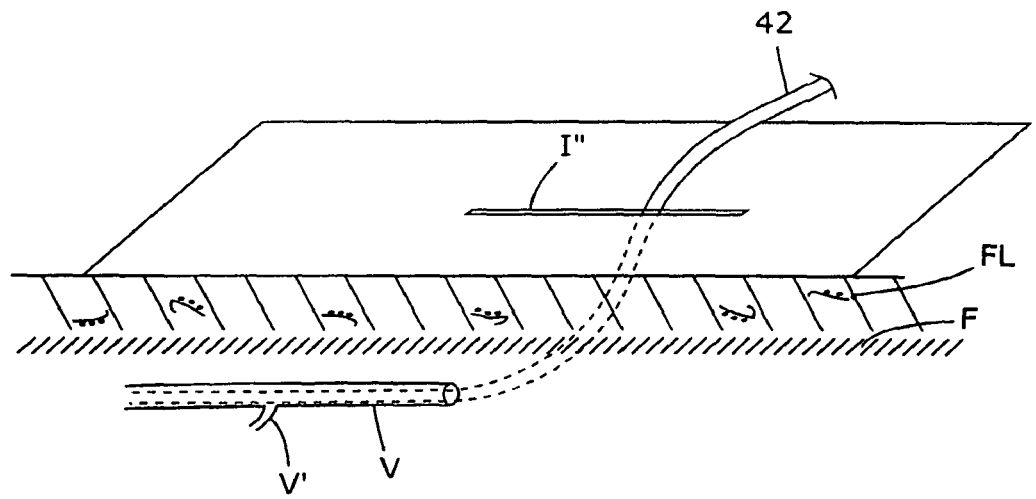
FIG. 4A is a partial cross-sectional view of a portion of a patient's body illustrating insertion of the light catheter into the vein to be harvested.
Figure 4B:
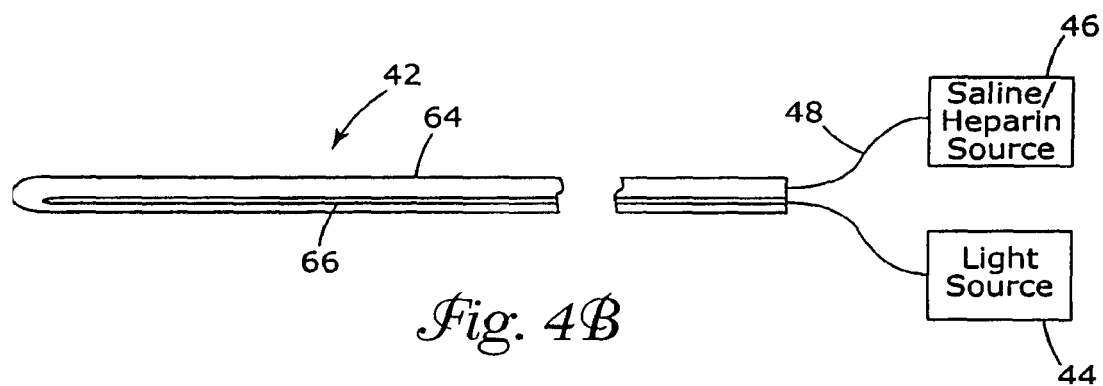
FIG. 4B is a partial plan view of the light catheter of the present invention.

As seen in FIGS. 4A and 4B light catheter 42 is inserted via distal incision I" into the saphenous vein at the distal end. Alternatively catheter 42 may be inserted into a large side branch located near the distal end of the vein. Light catheter 42 is moved proximally to the proximal end of the vein in the direction of incision I'. The construction of catheter 42 is best seen in FIG. 4B which is a partial view of catheter 42. Catheter 42 includes a transparent outer sheath 64 comprised of a material capable of transmitting light along the entire length of the catheter. A fiber optic cable 66 is connected to a light source 44. The catheter is constructed so that when inserted into a vein it will light up substantially the entire vein section being harvested and side branches along the length of the catheter. It should be understood that any light source sufficient to illuminate light catheter 42 along its length would be suitable for use in this invention. For example, light transmissive fluid or an internal chemical light source could be used. A heparin and/or saline source 46 is connected to the lumen of catheter 42 via line 48. Holes are provided in catheter 42 so that heparin and/or saline can be injected into the vein.

During a typical saphenous vein harvesting procedure the vein harvesting system is used as follows. A first incision I' is made over the groin area. A second distal incision I" is made above or below the knee depending on the length of vein needed. Expandable hood 10 is inserted into incision I' over the saphenous vein. The hood is expanded to create sufficient space to use the telescoping device including its dissecting and cutting tools. At the second incision the saphenous vein or a side branch is cut and light catheter 42 is inserted into the saphenous vein. Light catheter 42 is advanced in the proximal direction to a position sufficient to light the saphenous vein and side branches between the area of the first and second incisions. The telescoping device 20 is inserted beneath the hood through the first incision after the physician has exposed the saphenous vein with his or her finger. The saphenous vein is inserted into the vein dissector 32 through slot 62. The procedure is usually started with the telescoping device fully collapsed although the segments may be manipulated to lengthen the device if desired.

Figure 6:
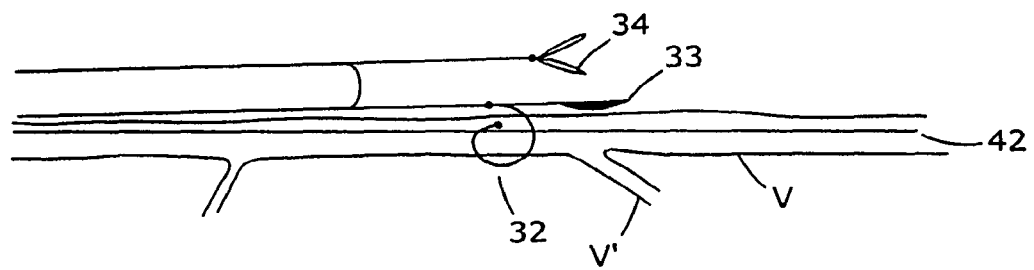
FIG. 6 is a partial view of the dissection process showing telescoping device used to dissect vein V and light catheter in the lumen of vein V.

The device is advanced under direct vision of the physician until no longer visible by eye, after which the physician views the process on the monitor. By utilizing light catheter 42 the physician's view of the dissection and cutting process is improved over prior art procedures where the light source is external to the vein. FIG. 6 shows the use of the telescoping device during the dissection of a vein containing the light catheter.

When a side branch is encountered the vein dissector is removed from the vein and the telescoping device rotated so that the bipolar scissors (or other cutting means) can be used to cut and coagulate (or clip) the side branch. The device is then rotated and the vein dissector slipped over the vein so the dissection process can continue.

When the telescoping device has been inserted to a distance where it becomes necessary to lengthen the device to continue the dissection the physician withdraws the device through the incision far enough so that the sections can be grasped and pulled apart to lengthen the device a desired amount. The device is then moved distally and the dissection process continued.

When a sufficient length of the vein has been dissected the device is removed from the first incision and the vein is cut at the location of the first and second incisions and then removed, usually from the first incision.

It should be appreciated that the light catheter could be inserted through the same incision as the telescoping device and inserted into the vessel through a side branch.

Although particular embodiments have been disclosed herein in detail, this has been done for purposes of illustration only, and is not intended to be limiting with respect to the scope of the claims. In particular, it is contemplated that various substitutions, alterations, and modifications may be made to the invention without departing from the spirit and scope of the invention as defined by the claims. In addition, it should be understood that although the various components and tools of this invention have been disclosed as a system it is possible and advantageous to use them separately. For example, the expandable hood of this invention could be used advantageously with known vein harvesting tools to create working space therefore. The telescoping device could be used without the expandable hood and could be used without the light catheter if provided with a light source. Further, the light catheter could advantageously be used to improve the use of prior art vein harvesting tools and techniques, the effectiveness of which would be enhanced by more clearly being able to visualize the vessel and side branches.

That which is claimed is:

1. A system for harvesting a section of a vessel from an incision in a human or animal body, the system comprising:
 a telescoping member having a first segment and a second segment, wherein the second segment is sized to fit within a lumen of the first segment, and wherein the second segment is adjustable to move from a first position in which a portion of the second segment is disposed within a portion of the first segment to a second position that is distal to the first position;
 a blunt tip extending distally relative to a distal end of the telescoping member, wherein the blunt tip tapers at a distal end;
 a cutting assembly associated with the second segment so that when the second segment is in the second position the cutting assembly is actuatable via an actuator to cut a blood vessel, wherein the cutting assembly is disposed off-center with respect to a central axis of the telescoping member; and an optic line disposed within the telescoping member so a dissection area is seeable via the optic line.

2. The system of claim 1, further comprising:

an optical viewing detector for viewing an area immediately adjacent the distal end of the telescoping member, wherein the optic line is a fiber optic line connected to the optical viewing detector.

3. The system of claim 1, further comprising:

an elongate tool comprising a curved portion at a distal region thereof for at east partially circumscribing the vessel section, wherein the elongate tool is inserted through the telescoping member.

4. The system of claim 1, wherein the cutting assembly is configured to cut and cauterize the blood vessel.

5. The system of claim 1, wherein the cutting assembly employs bipolar energy to cauterize the blood vessel.

6. The system of claim 1, wherein when the second segment is in the second position, some portion of the second segment extends out of the lumen of the first segment.

7. A system for harvesting a section of a vessel from an incision in a human or animal body, the system comprising:

a device made of rigid material and having a proximal end and a distal end, wherein the device includes a first segment and a second segment, wherein the second segment is sized to fit within a lumen of the first segment, and wherein the second segment is adjustable to move from a first position in which at least a portion of the second segment is disposed within a portion of the first segment to a second position that is distal to the first position;

a blunt tip extending distally relative to the distal end of the device, wherein the blunt tip tapers at a distal end;

a cutting assembly associated with the second segment so that when the second segment is in the second position the cutting assembly is actuatable via an actuator attached to the device made of rigid material to cut and cauterize a blood vessel, wherein the cutting assembly is disposed off-center with respect to a central axis of the device made of rigid material; and an optic line disposed within the device so a dissection area is seeable via the optic line.

8. The system of claim 7, wherein the cutting assembly employs bipolar energy to cauterize the blood vessel.

9. The system of claim 7, wherein when the second segment is in the second position, some portion of the second segment extends out of the lumen of the first segment.

10. The system of claim 7, wherein when the first segment is cylindrical and rigid.

11. The system of claim 10, wherein when the second segment is cylindrical and rigid.

12. The system of claim 7, wherein the rigid material is metal or plastic.

13. A system for harvesting a section of a vessel from an incision in a human or animal body, the system comprising:

a telescoping member having a first segment and a second segment, wherein the second segment is sized to fit within a lumen of the first segment, and wherein the second segment is adjustable to move from a first position in which a portion of the second segment is disposed within a portion of the first segment to a second position that is distal to the first position;

a blunt tip extending distally relative to a distal end of the telescoping member, wherein the blunt tip tapers at a distal end;

an optical path extending through the telescoping member to provide a view of a dissection area through the telescoping member; and a cutting assembly associated with the second segment so that when the second segment is in the second position the cutting assembly is actuatable via an actuator to cut a blood vessel in the view of the dissection area, wherein the cutting assembly is disposed off-center with respect to a central axis of the telescoping member.

14. The system of claim 13, wherein the optical path is provided by a fiber optic line.

15. A system for harvesting a section of a vessel from an incision in a human or animal body, the system comprising:

a device made of rigid material and having a proximal end and a distal end, wherein the device includes a first segment and a second segment, wherein the second segment is sized to fit within a lumen of the first segment, and wherein the second segment is adjustable to move from a first position in which at least a portion of the second segment is disposed within a portion of the first segment to a second position that is distal to the first position;

a blunt tip extending distally relative to the distal end of the device, wherein the blunt tip tapers at a distal end;

an optical path extending through the telescoping member to provide a view of a dissection area through the telescoping member; and a cutting assembly associated with the second segment so that when the second segment is in the second position the cutting assembly is actuatable via an actuator attached to the device made of rigid material to cut a blood vessel adjacent the distal end of the device that is in view through the optical path, wherein the cutting assembly is disposed off-center with respect to a central axis of the device made of rigid material.

16. The system of claim 15, wherein the optical path is provided by a fiber optic line.

17. A system for harvesting a section of a vessel from an incision in a human or animal body, the system comprising:

a telescoping member having a first segment and a second segment, wherein the second segment is sized to fit within a lumen of the first segment, and wherein the second segment is adjustable to move from a first position in which the second segment is disposed within the first segment to a second position that is distal to the first position;

a blunt tip extending distally relative to a distal end of the telescoping member, wherein the blunt tip tapers at a distal end;

an optical path extending through the telescoping member to provide a view of a dissection area through the telescoping member; and a cutting assembly associated with the second segment so that when the second segment is in the second position the cutting assembly is actuatable to cut a blood vessel in the view of the dissection area, wherein the cutting assembly is disposed off-center with respect to a central axis of the telescoping member.

18. The system of claim 17, wherein the optical path is provided by a fiber optic line.

19. A system for harvesting a section of a vessel from an incision in a human or animal body, the system comprising:

a telescoping member having a first segment and a second segment, wherein the second segment is sized to fit within a lumen of the first segment, and wherein the second segment is adjustable to move from a first position in which a portion of the second segment is disposed within a portion of the first segment to a second position that is distal to the first position;

a means of limiting axial movement of the first segment and the second segment relative to each other;

a blunt tip extending distally relative to a distal end of the telescoping member, wherein the blunt tip tapers at a distal end; and a cutting assembly associated with the second segment so that when the second segment is in the second position the cutting assembly is actuatable via an actuator to cut a blood vessel, wherein the cutting assembly is disposed off-center with respect to a central axis of the telescoping member.

20. The system of claim 19, wherein the means of limiting axial movement of the first segment and the second segment relative to each other comprises a dimple arranged to stop axial movement of the second segment at a distal most position relative to the first segment.

21. A system for harvesting a section of a vessel from an incision in a human or animal body, the system comprising:

a device made of rigid material and having a proximal end and a distal end, wherein the device includes a first segment and a second segment, wherein the second segment is sized to fit within a lumen of the first segment, and wherein the second segment is adjustable to move from a first position in which at least a portion of the second segment is disposed within a portion of the first segment to a second position that is distal to the first position;

a means of limiting axial movement of the first segment and the second segment relative to each other;

a blunt tip extending distally relative to the distal end of the device, wherein the blunt tip tapers at a distal end; and a cutting assembly associated with the second segment so that when the second segment is in the second position the cutting assembly is actuatable via an actuator attached to the device made of rigid material to cut a blood vessel, wherein the cutting assembly is disposed off-center with respect to a central axis of the device made of rigid material.

22. The system of claim 21, wherein the means of limiting axial movement of the first segment and the second segment relative to each other comprises a dimple arranged to stop axial movement of the second segment at a distal most position relative to the first segment.

* * * * *